US008846007B2

(12) United States Patent
Harvey

(10) Patent No.: US 8,846,007 B2
(45) Date of Patent: Sep. 30, 2014

(54) COMPOSITIONS PROVIDING A HEATING SENSATION FOR ORAL OR DERMAL DELIVERY

(75) Inventor: Joan E. Harvey, Morgantown, PA (US)

(73) Assignee: Intercontinental Great Brands LLC, East Hanover, NJ (US)

( * ) Notice: Subject to any disclaimer, the term of this patent is extended or adjusted under 35 U.S.C. 154(b) by 1839 days.

(21) Appl. No.: 11/644,105

(22) Filed: Dec. 22, 2006

(65) Prior Publication Data

US 2007/0148103 A1 Jun. 28, 2007

Related U.S. Application Data

(60) Provisional application No. 60/753,646, filed on Dec. 23, 2005.

(51) Int. Cl.
| | | |
|---|---|---|
| *A61K 8/00* | (2006.01) | |
| *A23G 4/06* | (2006.01) | |
| *A23L 1/226* | (2006.01) | |
| *A61Q 19/00* | (2006.01) | |
| *A61K 8/49* | (2006.01) | |
| *A61Q 11/00* | (2006.01) | |
| *A61K 8/34* | (2006.01) | |
| *A61K 8/42* | (2006.01) | |
| *A61K 8/97* | (2006.01) | |
| *A23G 3/42* | (2006.01) | |
| *A61K 8/33* | (2006.01) | |
| *A23G 1/32* | (2006.01) | |

(52) U.S. Cl.
CPC ....... *A23L 1/22614* (2013.01); *A61K 2800/592* (2013.01); *A23G 4/06* (2013.01); *A61Q 19/00* (2013.01); *A61K 8/49* (2013.01); *A61Q 11/00* (2013.01); *A23L 1/2265* (2013.01); *A61K 8/347* (2013.01); *A23L 1/22657* (2013.01); *A61K 8/42* (2013.01); *A61K 8/97* (2013.01); *A61K 2800/242* (2013.01); *A61K 2800/59* (2013.01); *A23G 3/42* (2013.01); *A61K 8/33* (2013.01); *A61K 2800/244* (2013.01); *A23G 1/32* (2013.01)
USPC ......................................................... 424/49

(58) Field of Classification Search
None
See application file for complete search history.

(56) References Cited

U.S. PATENT DOCUMENTS

| | | |
|---|---|---|
| 3,857,963 A | 12/1974 | Graff et al. |
| 3,897,566 A | 7/1975 | Bahoshy et al. |
| 3,930,026 A | 12/1975 | Clark |
| 4,032,661 A | 6/1977 | Rowsell et al. |
| 4,033,994 A | 7/1977 | Watson et al. |
| 4,059,118 A | 11/1977 | Watson et al. |
| 4,060,091 A | 11/1977 | Watson et al. |
| 4,070,449 A | 1/1978 | Rowsell et al. |
| 4,136,163 A | 1/1979 | Watson et al. |
| 4,193,936 A | 3/1980 | Watson et al. |
| 4,230,688 A | 10/1980 | Rowsell et al. |
| 4,271,197 A | 6/1981 | Hopkins et al. |
| 4,352,822 A | 10/1982 | Cherukuri et al. |
| 4,388,328 A | 6/1983 | Glass |
| 4,459,425 A | 7/1984 | Amano et al. |
| 4,485,118 A | 11/1984 | Carroll et al. |
| 4,497,832 A | 2/1985 | Cherukuri et al. |
| 4,568,560 A | 2/1986 | Schobel |
| 4,590,075 A | 5/1986 | Wei et al. |
| 4,722,845 A | 2/1988 | Cherukuri et al. |
| 4,751,095 A | 6/1988 | Karl et al. |
| 4,752,481 A | 6/1988 | Dokuzovic |
| 4,803,082 A | 2/1989 | Cherukuri et al. |
| 4,918,182 A | 4/1990 | Jackson et al. |
| 4,927,646 A | 5/1990 | Jenner et al. |
| 4,929,447 A | 5/1990 | Yang |
| 4,933,190 A | 6/1990 | Cherukuri et al. |
| 4,971,797 A | 11/1990 | Cherukuri et al. |
| 4,981,698 A | 1/1991 | Cherukuri et al. |
| 5,004,595 A | 4/1991 | Cherukuri et al. |
| 5,009,893 A | 4/1991 | Cherukuri et al. |
| 5,009,900 A | 4/1991 | Levine et al. |
| 5,041,294 A | 8/1991 | Patel |

(Continued)

FOREIGN PATENT DOCUMENTS

| | | |
|---|---|---|
| EP | 0 255 260 | 2/1988 |
| EP | 0 434 321 | 6/1991 |

(Continued)

OTHER PUBLICATIONS

Quantitative Model Studies on the Efficiency of Precursors in the Formation of Cooling-Active 1-Pyrrolidinyl-2-cyclopenten-1-ones and Bitter-Tasting Cyclopenta-[b]azepin-8 (1H)-ones; Journal of Agricultural and Food Chemistry; 2002; vol. 50; pp. 5156-5161.

(Continued)

*Primary Examiner* — Snigdha Maewall

(74) *Attorney, Agent, or Firm* — Cantor Colburn LLP

(57) ABSTRACT

The present invention relates to a heating or warming composition that may be delivered orally or to the skin or mucous membranes. The composition contains a warming agent in combination with a cooling agent. The warming agent and cooling agent may be provided in one composition or they may be provided separately in distinct formulations separated over time or geographically. The present invention also extends to methods of providing a heating sensation as well as to products for oral or skin or mucous membrane delivery that contain such a warming composition or that contain a warming agent in combination with a cooling agent. Such products include food products, beverages, chewing gums, confections, cosmetics, lotions, creams and the like containing such a warming composition.

7 Claims, No Drawings

(56) References Cited

U.S. PATENT DOCUMENTS

| | | | |
|---|---|---|---|
| 5,158,790 | A | 10/1992 | Witkewitz et al. |
| 5,244,670 | A | 9/1993 | Upson et al. |
| 5,266,335 | A | 11/1993 | Cherukuri et al. |
| 5,266,592 | A | 11/1993 | Grub et al. |
| 5,284,659 | A | 2/1994 | Cherukuri et al. |
| 5,372,824 | A | 12/1994 | Record et al. |
| 5,405,604 | A | 4/1995 | Hall |
| 5,407,665 | A | 4/1995 | McLaughlin et al. |
| 5,415,880 | A | 5/1995 | Song et al. |
| 5,429,827 | A | 7/1995 | Song et al. |
| 5,458,879 | A | 10/1995 | Singh et al. |
| 5,545,424 | A | 8/1996 | Nakatsu et al. |
| 5,603,971 | A | 2/1997 | Porzio et al. |
| 5,633,027 | A | 5/1997 | Cherukuri et al. |
| 5,725,865 | A | 3/1998 | Mane et al. |
| 5,744,180 | A | 4/1998 | Cherukuri et al. |
| 5,783,725 | A | 7/1998 | Kuhn et al. |
| 5,800,848 | A | 9/1998 | Yatka et al. |
| 6,159,509 | A | 12/2000 | Johnson et al. |
| 6,306,429 | B1 | 10/2001 | Bealin-Kelly |
| 6,379,652 | B1 | 4/2002 | Liu et al. |
| 6,623,266 | B2 | 9/2003 | Jani et al. |
| 6,627,233 | B1 | 9/2003 | Wolf et al. |
| 6,673,844 | B2 | 1/2004 | Kumamoto et al. |
| 6,780,443 | B1 | 8/2004 | Nakatsu et al. |
| 7,189,760 | B2 | 3/2007 | Erman et al. |
| 2002/0044968 | A1 | 4/2002 | Van Lengerich |
| 2002/0119231 | A1* | 8/2002 | Kumamoto et al. ........... 426/534 |
| 2002/0150616 | A1 | 10/2002 | Vandecruys |
| 2003/0215532 | A1* | 11/2003 | Nakatsu et al. ............... 424/734 |
| 2004/0238993 | A1 | 12/2004 | Benczedi et al. |
| 2005/0019445 | A1* | 1/2005 | Wolf et al. ......................... 426/3 |
| 2005/0196517 | A1 | 9/2005 | Hodanko et al. |
| 2007/0036733 | A1* | 2/2007 | Spence et al. ................... 424/48 |
| 2007/0048424 | A1 | 3/2007 | Moza et al. |

FOREIGN PATENT DOCUMENTS

| | | |
|---|---|---|
| EP | 0 453 397 | 10/1991 |
| EP | 0452273 | 10/1991 |
| EP | 1121927 | 8/2001 |
| EP | 1215258 | 6/2002 |
| EP | 0088067 | 12/2003 |
| EP | 1003475 | 1/2004 |
| GB | 1351761 | 5/1974 |
| JP | 01-206969 | 8/1989 |
| WO | WO 85/03414 | 8/1985 |
| WO | WO 90/04926 | 5/1990 |
| WO | WO 92/02145 | 2/1992 |
| WO | WO 93/23005 | 11/1993 |
| WO | WO 93/25177 | 12/1993 |
| WO | WO 95/07683 | 3/1995 |
| WO | WO 95/11671 | 4/1995 |
| WO | WO 96/03109 | 2/1996 |
| WO | WO 96/17524 | 6/1996 |
| WO | WO 97/02273 | 1/1997 |
| WO | WO 97/06695 | 2/1997 |
| WO | WO 97/24036 | 7/1997 |
| WO | WO 98/03076 | 1/1998 |
| WO | WO 98/47483 | 10/1998 |
| WO | WO 98/47484 | 10/1998 |
| WO | WO 98/52540 | 11/1998 |
| WO | WO 98/52545 | 11/1998 |
| WO | WO 99/13870 | 3/1999 |
| WO | WO 02/00039 | 1/2002 |
| WO | WO 03/063604 | 8/2003 |
| WO | WO 03/106404 | 12/2003 |
| WO | WO 2004/006967 | 1/2004 |
| WO | WO 2004/064544 | 8/2004 |
| WO | WO 2005/082154 | 9/2005 |
| WO | WO 2006/003349 | 1/2006 |
| WO | 2006020686 A1 | 2/2006 |
| WO | WO 2006/020686 * | 2/2006 |
| WO | WO 2006/039945 | 4/2006 |

OTHER PUBLICATIONS

Anonymous; "Caprol 3GO CAS No. 9007-48-1" XP002401201. Retrieved from the Internet: URL: http://www.abiteccorp.com/documents/3go-17_000.pdf> [retrieved on Sep. 28, 2006].

Anonymous; "HLB Systems" [Online] pp. 1-4, XP002401202. Retrieved from the Internet: URL: http://pharmacal.tripod.com/ch17.htm. [retrieved on Sep. 28, 2006].

Leffingwell, John C. "Cool without Menthol & Cooler than Menthol and Cooling Compounds as Insect Repellents." From the Internet: URL: http://www.leffingwell.com/cooler_than_menthol.htm [updated Apr. 5, 2006].

* cited by examiner ated than a heating or warming sensation delivered by a warming agent alone.

COMPOSITIONS PROVIDING A HEATING SENSATION FOR ORAL OR DERMAL DELIVERY

CROSS-REFERENCE TO RELATED APPLICATIONS

This application claims the benefit of U.S. Provisional Application No. 60/753,646, filed Dec. 23, 2005, the contents of which are incorporated herein by reference in their entirety.

FIELD

This invention relates to a warming composition that may be delivered orally or to the skin or mucous membranes. The composition contains a warming agent in combination with a cooling agent. The warming agent and cooling agent may be provided in one composition or they may be provided separately in distinct formulations separated over time or spatially.

BACKGROUND

Many substances are known to provide a sensation of warmth on application and are called "warming agents" or "heating agents". Exemplary warming agents include polyhydric alcohols, capsicum (red pepper) powder, a capsicum tincture, capsicum extract, capsaicin, homocapsaicin, homodihydrocapsaicin, nonanoyl vanillyl amide, nonanoic acid vanillyl ether, vanillyl alcohol alkyl ether derivatives such as vanillyl ethyl ether, vanillyl butyl ether, vanillyl pentyl ether, and vanillyl hexyl ether, isovanillyl alcohol alkyl ethers, ethylvanillyl alcohol alkyl ethers, veratryl alcohol derivatives, substituted benzyl alcohol derivatives, substituted benzyl alcohol alkyl ethers, vanillin propylene glycol acetal, ethylvanillin propylene glycol acetal, ginger extract, ginger oil, gingeol, and gingeron. Warming compositions may be added either directly or in the form of a flavor composition to food products, beverages, chewing gums, confections, cosmetics, lotions, creams and the like to produce a warming effect upon contact with sensory neurons on the skin or mucous membranes.

Many substances are known to provide a sensation of cooling on application and are called "cooling agents." Many compounds and compositions are known as cooling agents. Exemplary cooling agents include menthol, isopulegol, 3-(1-menthoxy)propane-1,2-diol, 3-(1-menthoxy)-2-methylpropane-1,2-diol, p-menthane-2,3-diol, p-menthane-3,8-diol, 6-isopropyl-9-methyl-1,4-dioxaspiro[4,5]decane-2-methanol, menthyl succinate and its alkaline earth metal salts, trimethylcyclohexanol, N-ethyl-2-isopropyl-5-methylcyclohexanecarboxamide, Japanese mint (Mentha arvensis) oil, peppermint oil, menthone, menthone glycerol ketal, menthyl lactate, 3-(1-menthoxy)ethan-1-ol, 3-(1-menthoxy)propan-1-ol, 3-(1-menthoxy)butan-1-ol, 1-menthylacetic acid N-ethylamide, 1-menthyl-4-hydroxypentanoate, 1-menthyl-3-hydroxybutyrate, N,2,3-trimethyl-2-(1-methylethyl)-butanamide, and spearmint oil.

In some instances, a cooling agent and a warming agent have been used together in a single product. For instance, U.S. Pat. No. 6,838,106 to Kumamoto et al., the disclosure of which is incorporated herein by reference, provides some formulations featuring some cooling agents in combination with some warming agents for use in food, drinks and oral care preparations. Likewise, U.S. Pat. No. 6,673,844 to Kumamoto et al., the disclosure of which is incorporated herein by reference, provides some formulations featuring some cooling agents in combination with some warming agents for use in topical, cosmetic or pharmaceutical products. Additionally, U.S. Pat. No. 6,306,429 to Bealin-Kelly et al. The disclosure of which is incorporated herein by reference, teaches throat drops having a warming agent geographically distinct from a cooling agent such that a heating sensation and a cooling sensation are generated in a manner that is distinct both in time and in the body location where they are perceived. Such throat drops function to provide differential perception of either a cooling or a heating sensation because the agents capable of generating such a sensation are spatially separated and dissolve in the mouth or throat at different points in time.

There is a need, however, for warming compositions that provide an enhanced and/or longer lasting heating sensation upon consumption or application to the skin.

SUMMARY

In some embodiments, there is provided a warming or heating composition including a cooling agent and a warming agent. The composition provides an enhanced warming effect. A combination of a cooling agent and a warming agent produces a warming sensation at a lower concentration than that at which each component alone is effective. In addition, a combination of a cooling agent and a warming agent produces a warming sensation that is longer lasting than that experienced from a warming agent alone. Further, providing a combination of a warming agent with a cooling agent allows shifting perception of the heating sensation either or both spatially or temporally. The warming agent and the cooling agent may be administered separately or in one single formulation.

In some embodiments, there is provided a chewing gum or confectionery composition including a warming or heating composition including a cooling agent and a warming agent. The chewing gum thereby features an enhanced warming effect. The warming agent and the cooling agent may be found within the chewing gum or confectionery separately or in one single formulation. As an added feature, a combination of a cooling agent and a warming agent may allow a chewing gum or confectionery providing a warming sensation with a lower concentration of warming agent than with a chewing gum having only a warming agent and no cooling agent. In addition, a chewing gum or confectionery composition may produce a warming sensation that is longer lasting than that experienced from a chewing gum having only a warming agent alone and no cooling agent. Further, the chewing gums and confectioneries may be characterized as providing a shifting perception of the heating sensation either or both spatially and temporally. The warming agent may be present in the chewing gum in an amount of, for instance, about 0.1 to 50% by weight of the composition, specifically about 0.5 to 10% by weight of the composition, more specifically about 1 to 5% by weight of the composition and even more specifically about 2.5 to about 4.0% by weight of the composition. The cooling agent may be present in the chewing gum in an amount of about 0.01 to about 5% by weight of the composition, specifically about 0.05 to about 2% by weight of the composition, and even more specifically about 0.1 to about 1% by weight of the composition.

In some embodiments, there is provided a method for delivering a warming sensation at a lower concentration of warming agent than the concentration of warming agent required to deliver a warming sensation alone.

In some embodiments, there is provided a method for delivering a heating or warming sensation that is longer lasting than the heating or warming sensation perceived when a warming agent is delivered without the presence of a cooling agent.

In some embodiments, there is provided a method of shifting the perception of a heating or warming sensation either or both spatially and temporally on a mucous membrane, such as, for instance, the mouth.

In some methods, the heat perception is either perceived in a geographical area of the oral cavity or mucous membrane that is shifted from where it would be perceived from a composition lacking a cooling agent, or the heat perception is longer in duration or of greater intensity than it would be from a composition, chewing gum or confectionery lacking such a cooling agent. In some embodiments, the heat perception is both of longer duration and it is perceived in a geographically shifted locale. All of these methods are accomplished by administering a warming composition or a chewing gum or confectionery composition as described herein.

In some embodiments, there is provided a warming or heating composition including: at least one warming agent which includes ginger in an amount of up to about 5% by weight of the composition, vanillyl butyl ether in an amount of about 15% to about 80% by weight of the composition, capsicum oleoresin in an amount of about 15% to about 55% by weight of the composition and piperine in an amount of about 0.00001% to about 35% by weight of the composition; and at least one cooling agent which includes menthol in an amount of up to about 2% by weight of the composition, N,2,3-trimethyl-2-isopropyl butanamide in an amount of up to about 1% by weight of the composition and N-ethyl-p-menthane-3-carboxamide in an amount of up to about 1% by weight of the composition. The warming composition provides an enhanced and longer lasting heating sensation as compared to the heating sensation provided by the composition in the absence of the at least one cooling agent.

DETAILED DESCRIPTION

The present invention is based in part upon the discoveries that providing a cooling agent in combination with a warming agent separately or in a single formulation provides a warming composition or a chewing gum or confectionery product with surprising benefits. Among these benefits include a longer lasting perception of heat that may be achieved with a lower amount of warming agent than would be required if the warming agent was present without a cooling agent. Likewise, a chewing gum or confectionery product containing such a heating or warming composition or a warming and cooling agent provided in distinct formulations features the ability to geographically or temporally shift the heating sensation. This may be accomplished without sequestering the warming agent and cooling agent so that they do not encounter their environment simultaneously. Rather, the warming agent and the cooling agent may be administered simultaneously in the same formulation or in separate formulations that encounter the environment at substantially the same time.

The present invention is further based in part upon the discovery that adding 100 to 5000 parts per million of a cooling agent to a warming agent composition or to a product containing a warming agent or warming agent composition produces an enhanced heat sensation that may be of longer duration and that may result in a geographical or physiological shift in the location where the heat sensation is perceived. Preferably, about 500 to 2000 parts per million of the cooling agent are added. In especially useful embodiments, addition of the cooling agent may result in a shift of the perception of heat from the tongue to the rear of the mouth or to the throat of an individual orally taking the warming composition or a product containing it.

As used herein the transitional term "comprising," (also "comprises," etc.) which is synonymous with "including," "containing," or "characterized by," is inclusive or open-ended and does not exclude additional, unrecited elements or method steps, regardless of its use in the preamble or the body of a claim.

As used herein, the terms "bubble gum" and "chewing gum" are used interchangeably and are both meant to include any chewing gum compositions.

As used herein, the term "confectionery base" includes any ingredient or group of ingredients that represent form the bulk of the confectionery composition and provide the confectionery composition with its structural integrity and to which other ingredients are added.

As used herein, the term "cooling agent" includes any agent whether described herein, known in the art as producing, or otherwise capable of producing a sensation described as cooling by those experiencing it on the skin, oral cavity or mucous membranes.

As used herein, the term "warming agent" (or "heating agent") includes any agent whether described herein, known in the art as producing, or otherwise capable of producing a sensation described as warming or imparting a sensation of heat by those experiencing it on the skin, oral cavity or mucous membranes.

As used herein, the term "spatial shift" in sensation is meant to refer to an alteration in the geographical or physiological position at which a sensation is normally perceived, for instance, a shift from a heat perception on the tongue to the throat or rear of the mouth.

As used herein, the term "temporal shift" in sensation is meant to refer to a delay in the perception of a sensation or a lengthening in the duration of the perception of a sensation.

Embodiments described herein provide warming or heating compositions that include a combination of at least one cooling agent and at least one warming agent. The warming compositions provide an enhanced and/or longer-lasting heating sensation as compared to such compositions in the absence of the cooling agent(s). Suitable cooling agents and warming agents for use in the warming compositions are described below.

Cooling Agents

In some embodiments of the warming composition is the presence of a physiological cooling agent. Physiological cooling agent encompasses any number of cooling agents. Suitable levels of the cooling agent are from about 0.001 to about 10%, by weight of the warming composition, specifically from about 0.01 to about 5% by weight of the warming composition, and more specifically from about 0.05 to about 3% by weight of the warming composition.

Cooling agents are well known in the art and are described in, for instance, U.S. Pat. Nos: 4,032,661, 4,070,449, 4,033, 994, 4,296,093, 4,296,255, 4,230,688, 4,034,109, 4,020,153, 4,136,163, 5,266,592, U.S. Publication Nos. 2004/0067970 and 2005/0019455, and a publication by John C. Leffingwell available at http://www.leffingwell.com, entitled "Cool without Menthol & Cooler than Menthol and Cooling Compounds as Insect Repellents," the disclosures of which are herein incorporated by reference. A test for physiological cooling agents is described in GB-A-1,452,291, published Oct. 13, 1976, reproduced in part herein below for convenience. In some embodiments, the cooling agents do not have a perceptible flavor of their own, but simply provide a cooling effect.

In such embodiments, as the cooling agents do not have their own perceptible flavor, they can be used with other types of flavors.

Several U.S. and foreign references disclose specific compounds and classes of compounds that are cooling agents that may be used in the warming compositions. Some of these disclose the use of cooling agents in chewing gum. These include, for instance, U.S. Pat. No. 5,451,404 (a ketal combined with another coolant (menthol or carboxamides)); U.S. Pat. No. 5,372,824 (physiological cooling agents and reduced menthol); U.S. Pat. No. 5,348,750 (menthone ketals); U.S. Pat. No. 5,326,574 (a spray dried 3-1-menthoxypropane-1,2-diol-); U.S. Pat. No. 5,266,592 (menthone glycerol ketals); U.S. Pat. No. 5,165,943 (a cyclodextrin complex with physiological cooling agents); U.S. Pat. No. 5,009,893 (p-menthane carboxamide physiological cooling agent with menthol for reduced bitterness); U.S. Pat. No. 4,459,425 (3-1-menthoxypropane-1,2-diol); U.S. Pat. No. 4,296,093 (substituted cyclohexanamides); U.S. Pat. Nos. 4,248,859 and 4,318,900 (alkyl substituted alicyclic carboxylic acids, esters or amides); U.S. Pat. Nos. 4,157,384 and 4,029,759 (various 3-substituted p-menthanes); U.S. Pat. No. 4,081,480 (alpha-oxy(oxo)mercaptan alkanes); U.S. Pat. No. 4,070,449 (sulphoxides and sulphones); U.S. Pat. Nos. 4,060,091; 4,190,643 and 4,136,163 (substituted p-menthane-3-carboxamides); U.S. Pat. Nos. 4,153,679; 4,296,255 and 4,230,688 (acyclic carboxamides); U.S. Pat. No. 4,034,109 (acyclic sulphonamides and sulphinamides); U.S. Pat. No. 4,033,994 (p-menthane-3-carboxylates); U.S. Pat. Nos. 3,793,446 and 3,644,613 (ketoesters of menthol); U.S. Pat. No. 3,720,762 (spilanthol with menthol or peppermint oil); Canadian Patent No. 2,101,790 (carbonic acids having free polar groups); German Patent No. 2,608,226 (menthyl lactate); German Patent No. 2,433,165 (N-acetylglycine menthyl ester); French Patent No. 2,577,922 (L-menthyl-3-hydroxybutyrate); Japanese Patent No. 94/065023 (2-isopropenyl-5-methylcyclohexanol); Great Britain Patent No. 1,502,680 (bicyclic acids, esters, amides and substituted menthanols); Great Britain Patent No. 1,476,351 (cyclic and acyclic amides, ureas and sulphonamides); Great Britain Patent No. 1,442,998 (trialkyl-substituted cyclohexane carboxamides); Great Britain Patent Nos. 1,421,744 and 1,421,743 (novel amides); Great Britain Patent No. 1,411,786 (cyclohexanamides); Great Britain Patent No. 1,404,596 (acyclic secondary and tertiary alkanols); PCT Publication No. WO 97/07771 (menthyl succinate and carboxamides); PCT Publication No. WO 96/28133 (coolant composition for comestibles); PCT Publication No. WO 96/17524 (a cooling composition comprising N-substituted p-menthane carboxamides and menthol); PCT Publication No. WO 94/010117 (cyclohexanol derivatives); and U.S. Pat. No. 3,639,569 (physiological cooling agents).

Particular examples of cooling agents include, for instance, substituted p-menthanes, substituted p-menthane-carboxamides (e.g., N-ethyl-p-menthane-3-carboxamide (FEMA 3455)), acyclic carboxamides, substituted cyclohexanamides, substituted cyclohexane carboxamides, substituted ureas and sulphonamides, and substituted menthanols (all from Wilkinson Sword); hydroxymethyl and hydroxyethyl derivatives of p-menthane (from Lever Bros.); menthyl succinate and its alkaline earth metal salts; 2-mercapto-cyclodecanone (from International Flavors and Fragrances); 2-isopropanyl-5-methylcyclohexanol (from Hisamitsu Pharmaceuticals, hereinafter "isopregol"); hydroxycarboxylic acids with 2-6 carbon atoms; menthone glycerol ketals (FEMA 3807, tradename FRESCOLAT.™. type MGA); 3-1-menthoxypropane-1,2-diol (from Takasago, FEMA 3784, (hereinafter "TCA")); and menthyl lactate; (from Haarman & Reimer, FEMA 3748, tradename FRESCOLAT® type ML).

Further useful cooling agents include xylitol, erythritol, dextrose, sorbitol, menthane, menthone, ketals, menthone ketals, mono menthyl glutarate, cyclohexanamides, menthyl acetate, menthyl salicylate, N,2,3-trimethyl-2-isopropyl butanamide (WS-23), N-ethyl-p-menthane-3-carboxamide (WS-3), isopulegol, 3-(1-menthoxy)propane-1,2-diol, 3-(1-menthoxy)-2-methylpropane-1,2-diol, p-menthane-2,3-diol, p-menthane-3,8-diol, 6-isopropyl-9-methyl-1,4-dioxaspiro[4,5]decane-2-methanol, trimethylcyclohexanol, N-ethyl-2-isopropyl-5-methylcyclohexanecarboxamide, Japanese mint oil, peppermint oil, 3-(1-menthoxy)ethan-1-ol, 3-(1-menthoxy)propan-1-ol, 3-(1-menthoxy)butan-1-ol, 1-menthylacetic acid N-ethylamide, 1-menthyl-4-hydroxypentanoate, 1-menthyl-3-hydroxybutyrate, N,2,3-trimethyl-2-(1-methylethyl)-butanamide, n-ethyl-t-2-c-6 nonadienamide, N,N-dimethyl menthyl succinamide, substituted p-menthanes, menthone glycerol ketals (FEMA 3807, tradename FRESCOLAT® type MGA); WS-30, WS-14, Eucalyptus extract (p-Mehta-3,8-Diol), Menthol (its natural or synthetic derivatives), Menthol PG carbonate, Menthol EG carbonate, Menthol glyceryl ether, N-tertbutyl-p-menthane-3-carboxamide, P-menthane-3-carboxylic acid glycerol ester, Methyl-2-isopryl-bicyclo (2.2.1), Heptane-2-carboxamide; and Menthol methyl ether, and menthyl pyrrolidone carboxylate among others. The cooling agents described here and other suitable cooling agents are further described in the following U.S. patents, all of which are incorporated in their entirety by reference hereto: U.S. Pat. Nos. 4,230,688; 4,032,661; 4,459,425; 4,136,163; 5,266,592; 6,627,233.

Other suitable cooling agents are described in International Publication No. WO97/06695. Some include menthol, peppermint oil, N-substituted-p-menthane-3-carboxamides, acyclic tertiary and secondary carboxamides, 3-1-menthoxy propan-1,2-diol and mixtures thereof. Some carboxamides found most useful are those described in U.S. Pat. No. 4,136,163, Jan. 23, 1979 to Watson et al., and U.S. Pat. No. 4,230,688, Oct. 28, 1980 to Rowsell et al. The carboxamides in U.S. Pat. No. 4,136,163 are N-substituted-p-menthane-3-carboxamides. N-ethyl-p-menthane-3-carboxamide is commercially available as WS-3 from Wilkinson Sword. The carboxamides of U.S. Pat. No. 4,230,688 are certain acyclic tertiary and secondary carboxamides, of which trimethyl isopropyl butanamide is commercially available as WS-23 from Wilkinson Sword. Others include WS-3, WS-14, WS-23 and the like.

The following test procedure can be used as a means to identify compounds having a physiological cooling activity. This test is intended purely as a means for identifying compounds having a physiological cooling agent activity and useful in the present invention and for giving an indication of the different relative activities of the compounds, as between themselves and as compared with menthol, when applied in particular manner to a particular part of the body. The results are not necessarily indicative of the activity of these compounds in other formulations and other parts of the body where other factors come into play. For example, a controlling factor in the onset of cooling effect, its intensity and longevity will be the rate of penetration of the compounds through the epidermis or mucous membrane, and this will vary in different locations on the human body. The formulation of actual products according to this invention will therefore be done largely on an empirical basis although the test results and other figures given herein will be useful as a guide, particularly in the formulation of products for oral administration, since the test procedure to be described involves oral application of the compound. A similar test may, of course, be devised for the purposes of measuring the relative activities of the compounds of another area of the body, for example, the face or forearm, and this will be a useful guide in the choice of compounds to be used in preparations for external topical usage. It will also be noted that the described test procedure is done on a statistical basis. This is necessary since sensitivity to these compounds will vary not only from compound to compound and from one part of the body to another, but also from one individual to another. Tests of this nature are commonly used in the testing of the organoleptic properties, e.g. taste and smell of organic and inorganic compounds, see Kirk-Othmer: Encyclopedia of Chemical Technology, 2nd Ed. (1967) Vol. 14, pages 336-344.

The following test procedure is aimed at determining the minimum quantity of the test compound required to produce a noticeable cooling effect in a person of average sensitivity, this minimum quantity being termed the threshold for that particular compound. The tests are carried out on a selected panel of 6 people of median sensitivity to 1-menthol.

To select a test panel of average sensitivity the following procedure is used. Known quantities of 1-menthol in solution in petroleum ether (bp. 40-60° C.) are placed on 5 mm squares of filter paper, after which the solvent is allowed to evaporate. A panel of observers is enrolled and asked to place one impregnated square at a time on the tongue and to report on the presence or absence of a cooling effect. The quantity of 1-menthol on each impregnated square is gradually reduced from a value substantially above 0.25 micrograms per square to substantially below 0.25 micrograms, the precise range being immaterial. Conveniently, one starts with squares containing 2.0 micrograms being half that of the preceding square, i.e. the second test square will contain 1.0 microgram, the third 0.5 microgram, and so on. Each quantity is tested on the tongue at least 10 times. In this way, the thresholds to cold receptor stimulus by 1-menthol are determined for each individual of the panel, the threshold for each individual being that amount of 1-menthol for which, in a series of not less than 10 test applications, a cooling effect is reported 50% of the time. Six panel members are now selected whose threshold to 1-menthol is in the range 0.1 micrograms to 10 micrograms and whose average threshold is approximately 0.25 micrograms, this select panel being regarded as the test panel of average sensitivity.

To test the activity of cooling agents, the above procedure is repeated using only the 6 selected panel members of average sensitivity to 1-menthol. The individual thresholds for each test compound on each of the 6 selected panel members are determined and averaged. Those compounds whose average threshold on the select test panel is 100 micrograms or less, preferably 50 micrograms or less are regarded as having cooling activity in accordance with this invention.

The cooling agent used in the warming compositions of some embodiments may be any compound or composition known as a cooling agent. Typical examples of the cooling agents which can be used in the compositions described herein include:

(1) a compound represented by formula (I):

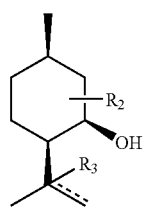

(I)

wherein $R^2$ and $R^3$ each represent a hydrogen atom or a hydroxyl group, ----- represents a single bond or a double bond, the same definition applies hereinafter;

(2) a compound represented by formula (II):

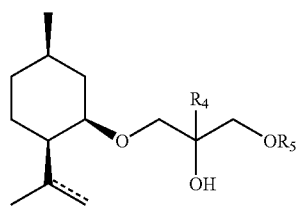

(II)

wherein $R^4$ represents a hydrogen atom or a methyl group, $R^5$ represents a hydrogen atom, a lower alkyl group or a 2-alkoxyethyl group;

(3) a compound represented by formula (III):

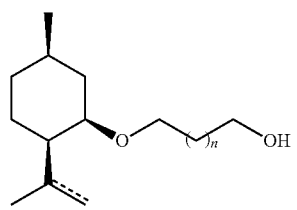

(III)

wherein n represents an integer of 1 to 10;

(4) a compound represented by formula (IV):

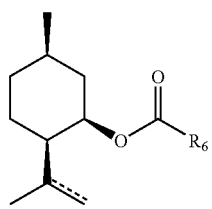

(IV)

wherein $R^6$ represents a hydrogen atom, a straight-chain or branched alkyl or alkenyl group, or a straight-chain or branched hydroxyalkyl group;

(5) 1-menthylacetic acid N-ethylamide; and
(6) N,2,3-trimethyl-2-(1-methylethyl)-butanamide.

Specific examples of cooling agents which may be used in the warming compositions include, but are not limited to, menthol, isopulegol, 3-(1-menthoxy)propane-1,2-diol, 3-(1-menthoxy)-2-methylpropane-1,2-diol, p-menthane-2,3-diol, p-menthane-3,8-diol, 6-isopropyl-9-methyl-1,4-dioxaspiro [4,5]decane-2-methanol, menthyl succinate and its alkaline earth metal salts, trimethylcyclohexanol, N-substituted-p-menthane-3-carboxamides, acyclic tertiary and secondary carboxamides, N-ethyl-2-isopropyl-5-methylcyclohexanecarboxamide, Japanese mint (Mentha arvensis) oil, peppermint oil, menthone, menthone glycerol ketal, menthyl lactate, 3-(1-menthoxy)ethan-1-ol, 3-(1-menthoxy)propan-1-ol, 3-(1-menthoxy)butan-1-ol, 1-menthylacetic acid N-ethylamide, 1-menthyl-4-hydroxypentanoate, 1-menthyl-3-hydroxybutyrate, N,2,3-trimethyl-2-(1-methylethyl)-butanamide, WS-3, WS-12, WS-14, N,2,3-trimethyl-2-isopropyl butanamide (WS-23) and spearmint oil. Mixtures of cooling agents also may be employed.

Particularly suitable cooling agents for use in the warming compositions described herein may include, for example, 3-(1-menthoxy)propane-1,2-diol, 3-(1-menthoxy)-2-methylpropane-1,2-diol, p-menthane-3,8-diol, 3-(1-menthoxy)ethan-1-ol, 3-(1-menthoxy)propan-1-ol, and 3-(1-menthoxy)butan-1-ol. Particularly desirable are 3-(1-menthoxy)propane-1,2-diol, 3-(1-menthoxy)-2-methylpropane-1,2-diol, N-ethyl-p-menthane-3-carboxamide, N,2,3-trimethyl-2-(1-methylethyl)-butanamide, and trimethyl isopropyl butanamide.

Warming Agents

In some embodiments, the warming composition includes a physiological warming agent (also referred to as "heating agent"). Suitable levels of the warming agent are from about 0.001 to about 10% by weight of the warming composition, specifically from about 0.01 to about 5% by weight of the warming composition, and more specifically from about 0.05 to about 3% by weight of the warming composition.

Warming agents can be tested by using a modification of the test for cooling agents described above, the test being modified to use benzyl alcohol rather than menthol as the reference sample and asking the panelists to report on the presence or absence of a warming effect rather than a cooling effect.

Suitable warming agents include those known in the art. Exemplary warming agents include, but are not limited to, vanillyl alcohol, vanillyl alkyl or alkenyl ethers represented by formula (V):

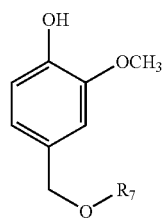

(V)

wherein $R^7$ represents a hydrogen atom or a straight chain or branched alkyl or alkenyl group having 1 to 10 carbon atoms, desirably 1 to 6 carbon atoms, such as vanillyl ethyl ether, vanillyl propyl ether, vanillyl butyl ether, vanillyl pentyl ether, and vanillyl hexyl ether; vanillin propylene glycol acetal; ethylvanillin propylene glycol acetal; compounds represented by formula (VI):

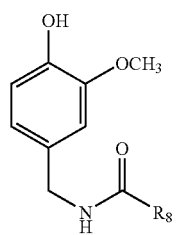

(VI)

wherein $R^8$ represents a straight-chain or branched alkyl or alkenyl group; gingeron; 4-(1-menthoxymethyl)-2-(3',4'-dihydroxyphenyl)-1,3-dioxolane; 4-(1-menthoxymethyl)-2-(2'-hydroxy-3'-methoxyphenyl)-1,3-dioxolan; capsicum tincture; and ginger extract.

Examples of suitable warming agents include, but are not limited to: vanillyl alcohol n-butyl ether, vanillyl alcohol n-propyl ether, vanillyl alcohol isopropyl ether, vanillyl alcohol isobutyl ether, vanillyl alcohol n-amino ether, vanillyl alcohol isoamyl ether, vanillyl alcohol n-hexyl ether, vanillyl alcohol methyl ether, vanillyl alcohol ethyl ether, gingerol, shogaol, paradol, zingerone, capsaicin, dihydrocapsaicin, nordihydrocapsaicin, homocapsaicin, homodihydrocapsaicin, ethanol, iso-propyl alcohol, iso-amylalcohol, benzyl alcohol, glycerine, chloroform, eugenol, cinnamon oil, cinnamic aldehyde, phosphate derivatives thereof, and the commercially available warming agent David Michael Heat, available from David Michael & Co., Inc., 10801 Decatur Road, Philadelphia, Pa. 19154, USA. The phosphate derivatives mentioned are those described in WO 97/02273, incorporated by reference herein. Mixtures of warming agents also may be employed in some embodiments.

Particularly suitable warming agents for use in the warming compositions of some embodiments include vanillyl ethyl ether, vanillyl propyl ether, vanillyl butyl ether, vanillyl pentyl ether, vanillyl hexyl ether, gingeron, capsicum tincture, and ginger extract. In some desirable embodiments, the warming agent may be vanillyl butyl ether, vanillyl pentyl ether, vanillyl hexyl ether, or capsicum tincture.

Warming Compositions

As described above, the warming compositions include a combination of at least one warming agent and at least one cooling agent. The cooling agent enhances and/or lengthens the warming effect provided by the compositions upon consumption or application to the skin. Any of the warming agents and cooling agents set forth above may be used. The warming composition also may include a carrier, such as water or a bulk sweetener, described in more detail below.

For instance, the warming composition may be diluted with a diluent safe to a human body, such as ethanol or pure water at an appropriate dilution decided according to the intended use, for example, about 1:2 to 1:10000. The warming agent may be present in an amount of, for instance, 0.1 to 50 wt. %, specifically 0.5 to 10 wt. %, more specifically 1 to 5 wt. % and even more specifically about 2.5 to about 4.0 wt. %. The cooling agent may be present in an amount of 0.01 to about 10 wt. %, specifically about 0.05 to about 7 wt. %, more specifically about 0.1 to about 5 wt. %, and even more specifically about 0.2 to about 3 wt. %.

For oral delivery preparations, the warming composition can be incorporated into a flavor composition. The flavor composition is not particularly limited, and any flavorings known in the art for use in foods, beverages or oral care products can be used. Examples of suitable flavorings include citrus flavors, such as an orange flavor, a lemon flavor, a lime flavor, a grapefruit flavor, a yuzu (Chinese lemon) flavor, and a sudachi flavor; fruit flavors, such as an apple flavor, a grape flavor, a strawberry flavor, a pineapple flavor, a banana flavor, a peach flavor, a melon flavor, an apricot flavor, an ume (Japanese apricot) flavor, a cherry flavor, a raspberry flavor, a blueberry flavor, and a tropical fruit flavor; milk flavors, such as a milk flavor, a butter flavor, a cheese flavor, a cream flavor, and a yogurt flavor; a vanilla flavor; tea or coffee flavors, such as a green tea flavor, a oolong tea flavor, a tea flavor, a cocoa flavor, a chocolate flavor, and a coffee flavor; mint flavors, such as a peppermint flavor, a spearmint flavor, and a Japanese mint flavor; spicy flavors, such as an asafetida flavor, an ajowan flavor, an anise flavor, an angelica flavor, a fennel flavor, an allspice flavor, a cinnamon flavor, a camomile flavor, a mustard flavor, a cardamon flavor, a caraway flavor, a cumin flavor, a clove flavor, a pepper flavor, a coriander flavor, a sassafras flavor, a savory flavor, a Zanthoxyli Fructus flavor, a perilla flavor, a juniper berry flavor, a ginger flavor, a star anise flavor, a horseradish flavor, a thyme flavor, a tarragon flavor, a dill flavor, a capsicum flavor, a nutmeg flavor, a basil flavor, a marjoram flavor, a rosemary flavor, a bayleaf flavor, and a wasabi (Japanese horseradish) flavor; meat flavors, such as a beef flavor, a pork flavor, and a chicken flavor; marine flavors, such as a fish flavor, a shell flavor, a crustacean flavor, a dried and smoked fishes flavor, and a seaweed flavor; alcoholic flavors, such as a wine flavor, a whisky flavor, a brandy flavor, a rum flavor, a gin flavor, and a liqueur flavor; floral flavors; and vegetable flavors, such as an onion flavor, a garlic flavor, a cabbage flavor, a carrot flavor, a celery flavor, mushroom flavor, and a tomato flavor. For the details of compositions of these flavors, refer to Japanese Patent Office Gazette 12(2000)-1[7270], Known and Customary Techniques (Perfumes), II. Food Flavors. The warming composition can be used as a blending component or an additive component in flavor blending or as an additive after blending.

The warming composition or the flavor composition can be used as an additive component to various products. The content of the warming composition in a final product is subject to wide variation according to the kind of the product, the amount of the product to be applied, the mode of use or application of the product, and the like.

The warming composition can be used in any compositions intended for oral, skin or mucosal delivery as a component for providing sensation of warmth, for prolonging the sensation of warmth, or for shifting the perception of warmth in time or geography. The products to which the warming composition is applicable include, but are not limited to, food and drink, such as candies, drops, chewing gums, tablets, chocolates, cakes, cookies, snack food, bread, tea, coffee, juice, fruit drinks, fruit wine, dairy drinks, carbonated beverages, alcoholic beverages, seasonings, salad dressings, and dips; and oral care preparations, such as mouthwash, toothpaste, nebulizers, drinks, medicinal drops, gargles, and chewables.

In addition to the warming composition, these products can contain other additives according to use. For example, additives permitted by Food Sanitation Law can be added to food and drink according to necessity. Useful additives include saccharides, sweeteners, inorganic salts, emulsifiers, acidifiers, flavorings, colors, antioxidants, raising agents, thickeners, vegetable oils, milk, and other dairy products. In general, bakery products can include wheat flour (base), butter, a raising agent, e.g., baking powder, an emulsifier, e.g., a sucrose fatty acid ester, saccharides, e.g., sugar, inorganic salts, and flavorings. Chocolate can include cacao mass (base) cacao butter, saccharides, e.g., sugar, milk, and an emulsifier. Emulsified dressings can include salad oil, water, vinegar, sugar, thickening polysaccharides, and sweeteners. Chewing gum can include a chewing gum base, saccharides, such as sugar, glucose and starch syrup, and flavors. Candy can include saccharides, acidifiers, e.g., citric acid, sweeteners, flavorings, and colors. Orange fruit drinks can include orange juice, sweeteners, e.g., isomerized sugars, acidifiers, e.g., citric acid, and antioxidants, e.g., vitamin C. Fruit milk drinks can comprise fruit juice, dairy products such as milk and powdered skim milk, saccharine, e.g., sugar, stabilizers, e.g., carboxymethyl cellulose, acidifiers (also known as food acids), e.g., citric acid, and flavorings, e.g., a pineapple flavor. In some embodiments, food acids and/or salts (or ingredients providing a salty taste) further enhance the intensity and/or longevity of the heating or warming sensation.

In particular embodiments, as will be described in more detail below, the warming compositions are used in chewing gums. Some chewing gum formulations are described in, for instance, U.S. Pat. Nos: 6,627,233, 6,685,916 and 6,696,044, herein incorporated by reference.

Additives which can be used in the preparations include inorganic salts, inorganic oxides, organic salts, thickeners, wetting agents, emulsifiers, surface active agents, humectants, alcohols, color additives, flavorings, and, if desired, medical ingredients such as crude drugs, hemostatics, circulation stimulants, antiinflammatory agents, astringents, antibacterial and/or antifungal agents, and bactericides. For example, toothpaste can comprise abrasives, such calcium phosphate, as calcium carbonate, aluminum hydroxide, silica, and calcium pyrophosphate; wetting agents, such as glycerin, sorbitol, and propylene glycol; tackifiers, such as carboxymethyl cellulose, carrageenan, and hydroxyethyl cellulose; surface active agents, such as sodium laurylsulfate, N-acylglutaminates, and sucrose fatty acid esters; sweeteners, such as saccharin sodium, stevioside, and xylitol; and medicinal components, such as vitamin E, azulene, aluminum chlorohydroxy allanthoinate, dextranase, hinokitiol, lysozyme chloride, and chlorhexidine.

Food acids can include, but are not limited to acetic acid, adipic acid, ascorbic acid, butyric acid, citric acid, formic acid, fumaric acid, glyconic acid, lactic acid, phosphoric acid, malic acid, oxalic acid, succinic acid, tartaric acid, aspartic acid, benzoic acid, caffeotannic acid, iso-citric acid, citramalic acid, galacturonic acid, glucuronic acid, glyceric acid, glycolic acid, ketoglutaric acid, a-ketoglutaric acid, lactoisocitric acid, oxalacetic acid, pyruvic acid, quinic acid, shikimic acid, succinic acid, tannic acid, hydroxyacetic acid, suberic acid, sebacic acid, azelaic acid, pimelic acid, capric cid, and combinations thereof.

Salts providing salty taste can include sodium chloride and/or potassium chloride. Salty taste can also be provided by ingredients such as yeast extracts, protein hydrolysates, soy sauce, and the like.

In some embodiments provided herein, the warming composition includes: at least one warming agent which includes ginger in an amount of up to about 5% by weight of the composition, vanillyl butyl ether in an amount of about 15% to about 80% by weight of the composition, capsicum oleoresin in an amount of about 15% to about 55% by weight of the composition and piperine in an amount of about 0.00001% to about 35% by weight of the composition; and at least one cooling agent which includes menthol in an amount of up to about 2% by weight of the composition, N,2,3-trimethyl-2-isopropyl butanamide in an amount of up to about 1% by weight of the composition and N-ethyl-p-menthane-3-carboxamide in an amount of up to about 1% by weight of the composition.

Chewing Gum Compositions

In some embodiments, the warming compositions described above are used in chewing gums. Compositions of chewing gum are well known in the art and described in depth in, for instance, U.S. Pat. Nos: 6,685,916, 6,627,233 and 6,696,044, the disclosures of which are incorporated by reference and some of which is summarized herein.

As used herein, the term "chewing gum" is meant to include any chewing gum compositions. Chewing gum compositions typically include one or more of chewing gum bases, flavoring agent and bulk sweeteners. The chewing gum compositions may be coated or uncoated and be in the form of slabs, sticks, pellets, balls and the like. The formulation of the different forms of the chewing gum compositions will be similar but may vary with regard to the ratio of the ingredients. For example, coated chewing gum compositions may contain a lower percentage of softeners. Pellets and balls have a small chewing gum core, which is then coated with either a sugar solution or a sugarless solution to create a hard shell. Slabs and sticks are usually formulated to be softer in texture than the chewing gum core. In order to overcome any detrimental softening effect the surfactant active may have on the chewing gum base, it is desirable to formulate a slab or stick chewing gum having a firmer texture (i.e. with less softener than is typically employed).

The warming or heating composition may be used in either regular chewing gum or bubble gum. Centerfilled chewing gum is another common chewing gum form in which the warming or heating composition may be used. The chewing gum portion has a similar composition and mode of manufacture to that described above. However, the centerfill is typically an aqueous solution or gel, which is injected into the center of the chewing gum during processing. The warming or heating compositions or heating agents and cooling agents could optionally be incorporated together or singly into the centerfill during manufacture of the fill or into the chewing gum. The centerfill chewing gum may also be optionally coated and may be prepared in various forms such as in the form of a lollipop.

In some embodiments, it is desirable to use a coated chewing gum in which the combination of heating and cooling agents or warming or heating compositions is in at least one of the core and the coating.

The chewing gum composition of some embodiments includes a chewing gum base and other typical chewing gum composition components such as sweeteners, softeners, flavoring agents and the like. The chewing gum composition may contain a reduced amount of softening agents such as lecithin or glycerin or may eliminate softeners. In addition, the chewing gum composition may contain a larger or smaller amount of sugar alcohols than conventional chewing gum compositions to facilitate delivery.

In accordance with one aspect of the chewing gum composition, the warming composition is added during the manufacture of the chewing gum composition, that is, with the sweeteners, flavoring agents and the like.

In a further aspect of the invention, the chewing gum base generally includes elastomers, elastomer plasticizers, waxes, fats, oils, emulsifiers, fillers, texturizers and may include a desirable combination of the heating and cooling agents or warming composition, as described above. Elastomers constitute from about 5% to 95% by weight of the chewing gum base, specifically about 10% to 70% by weight and more specifically about 15% to 45% by weight of the chewing gum base. The elastomer may be any water-insoluble polymer known in the art and includes those chewing gum polymers utilized for chewing gums and bubble gums. Illustrative examples of suitable polymers in chewing gum bases include both natural and synthetic elastomers. Examples of elastomers include synthetic elastomers such as polyisobutylene, polybutylene, isobutylene-isoprene co-polymers, styrene-butadiene co-polymers, polyvinylacetate and the like. Elastomers may also include natural elastomers such as natural rubber as well as natural chewing gums such as jelutong, lechi caspi, perillo, massaranduba balata, chicle, gutta hang kang or mixtures thereof. Other elastomers are known to those of ordinary skill in the art.

Elastomer plasticizers modify the firmness of the finished chewing gum when used in the chewing gum base. Elastomer plasticizers are typically present in an amount of up to about 75% by weight of the chewing gum base, specifically from about 5% to 45% by weight and more specifically from about 10% to 30% by weight of the chewing gum base. Examples of elastomer plasticizers include natural rosin esters such as glycerol ester of partially hydrogenated rosin, glycerol ester of tall oil rosin, pentaerythritol esters of partially hydrogenated rosin, methyl and partially hydrogenated methyl esters of rosin, and the like. Synthetic elastomer plasticizers such as terpene resins may also be employed in the chewing gum base composition.

Waxes include synthetic and naturally occurring waxes such as polyethylene, bees wax, carnauba and the like. Petroleum waxes such paraffin may also be used. When present in the chewing gum base, the waxes employed will have a melting point below 60° C. and preferably between about 45° C. and about 55° C. The waxes may be present in the amount of up to about 30% by weight of the chewing gum base. However, typically, the wax may be present in the chewing gum base in an amount from about 6% to about 10%, and more specifically from about 7% to about 9.5% by weight of the chewing gum base. Waxes aid in the curing of the finished chewing gum and help improve the release of flavor and may extend the shelf life of the product.

The chewing gum base may also include emulsifiers which aid in dispersing the immiscible components into a single stable system. The emulsifiers useful in this invention include glyceryl monostearate, lecithin, fatty acid monoglycerides, diglycerides, propylene glycol monostearate, and the like, and mixtures thereof. The emulsifier may be employed in amounts from about 2% to about 15%, and more specifically, from about 7% to about 11%, by weight of the chewing gum base.

Fillers modify the texture of the chewing gum base and aid processing. Examples of such fillers include calcium carbonate, magnesium carbonate, aluminum hydroxide, magnesium and aluminum silicates, clay, alumina, talc, titanium oxide, cellulose polymers, tricalcium phosphate, dicalcium phosphate, calcium sulfate, and the like. Fillers are typically present in an amount of from 1% to 60% by weight. Desirably, the amount of filler, when used, will be present in an amount from about 15% to about 40% and more specifically from about 20% to about 30%, by weight of the chewing gum base.

The chewing gum base may include plasticizers or softeners to provide a variety of desirable textures and consistency properties. Examples of softeners used in the chewing gum base include hydrogenated and partially hydrogenated vegetable oils, cocoa butter, glycerol monostearate, glycerol triacetate, di- and triglycerides, fatty acids such as stearic acid, palmitic acid, oleic acid, linoleic acid, linolenic acid and the like. The plasticizers and softeners are generally employed in the chewing gum base in amounts of up to about 20% by weight of the chewing gum base. Softeners in the chewing gum compositions are typically present in amounts of from about 0.5% to 10% by weight based on the total weight of the chewing gum composition.

The chewing gum base constitutes between 5% and 95% by weight of the chewing gum composition, more typically 10% to 50% by weight, and most typically from about 25% to 35% by weight of the chewing gum. A higher amount of chewing gum base is desirable.

A variety of traditional ingredients may be optionally included in the chewing gum base in effective amounts such as flavor agents and coloring agents, antioxidants, preservatives, and the like. For example, titanium dioxide and other dyes suitable for food, drug and cosmetic applications, known as F. D. & C. dyes, may be utilized. An anti-oxidant such as butylated hydroxytoluene (BHT), butylated hydroxyanisole (BHA), propyl gallate, vitamin E and mixtures thereof, may also be included. Other conventional chewing gum additives known to one having ordinary skill in the chewing gum art may also be used in the chewing gum base.

The chewing gum compositions may include amounts of conventional additives selected from the group consisting of sweetening agents, plasticizers, softeners, emulsifiers, waxes, fillers, bulking agents (carriers, extenders, bulk sweeteners), mineral adjuvants, flavor agents and coloring agents, antioxidants, acidulants, thickeners, medicaments, oral care actives, such as remineralization agents, antimicrobials and tooth whitening agents, as described in assignee's co-pending U.S. patent application Ser. No. 10/901,511, filed on Jul. 29, 2004 and entitled "Tooth Whitening Compositions and Delivery Systems Therefor," which is incorporated herein by reference in its entirety, and the like, and mixtures thereof. Some of these additives may serve more than one purpose. For example, in sugarless chewing gum compositions, a sweetener, such as maltitol or other sugar alcohol, may also function as a bulking agent.

Sweeteners suitable for use in the chewing gum compositions include both natural and artificial and both sugars and sugarless bulk sweeteners. Bulk sweeteners may be present in amounts of about 5% to about 99% by weight of the chewing gum composition. Sweeteners are typically present in the chewing gum compositions in amounts of from about 20% to 80% by weight, specifically from about 30% to 60% by weight. High intensity sweeteners such as sucralose, aspartame, neotame, salts of acesulfame, and the like are typically present up to about 1.0% by weight.

Suitable sugar sweeteners include mono-saccharides, di-saccharides and poly-saccharides such as but not limited to, sucrose (sugar), dextrose, maltose, dextrin, xylose, ribose, glucose, mannose, galactose, fructose (levulose), invert sugar, fructo oligo saccharide syrups, partially hydrolyzed starch, corn syrup solids and mixtures thereof.

Suitable sugarless bulk sweeteners include sugar alcohols (or polyols) such as, but not limited to, sorbitol, xylitol, mannitol, galactitol, maltitol, hydrogenated isomaltulose (ISOMALT), lactitol, erythritol, hydrogenated starch hydrolysates, and mixtures thereof.

Suitable hydrogenated starch hydrolysates include those disclosed in U.S. Pat. No. 4,279,931 and various hydrogenated glucose syrups and/or powders which contain sorbitol, maltitol, hydrogenated disaccharides, hydrogenated higher polysaccharides, or mixtures thereof. Hydrogenated starch hydrolysates are primarily prepared by the controlled catalytic hydrogenation of corn syrups. The resulting hydrogenated starch hydrolysates are mixtures of monomeric, dimeric, and polymeric saccharides. The ratios of these different saccharides give different hydrogenated starch hydrolysates different properties. Mixtures of hydrogenated starch hydrolysates, such as LYCASIN®, a commercially available product manufactured by Roquette Freres of France, and HYSTAR®, a commercially available product manufactured by SPI Polyols, Inc. of New Castle, Del., are also useful.

In some embodiments, high-intensity sweeteners may be used. Without being limited to particular sweeteners, representative categories and examples include:

(a) water-soluble sweetening agents such as dihydrochalcones, monellin, stevia, steviosides, rebaudioside A, glycyrrhizin, dihydroflavenol, and sugar alcohols such as sorbitol, mannitol, maltitol, xylitol, erythritol and L-aminodicarboxylic acid aminoalkenoic acid ester amides, such as those disclosed in U.S. Pat. No. 4,619,834, which disclosure is incorporated herein by reference, and mixtures thereof;

(b) water-soluble artificial sweeteners such as soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (Acesulfame-K), the free acid form of saccharin, and mixtures thereof;

(c) dipeptide based sweeteners, such as L-aspartic acid derived sweeteners, such as L-aspartyl-L-phenylalanine methyl ester (Aspartame) and materials described in U.S. Pat. No. 3,492,131, L-alphaaspartyl-N-(2,2,4,4-tetramethyl-3-thietanyl)-D-alaninamide hydrate (Alitame), N-[N-(3,3-dimethylbutyl)-L-aspartyl]-L-phenylalanine 1-methyl ester (Neotame), methyl esters of L-aspartyl-L-phenylglycerine and L-aspartyl-L-2,5-dihydrophenyl-glycine, L-aspartyl-2,5-dihydro-L-phenylalanine; L-aspartyl-L-(1-cyclohexen)-alanine, and mixtures thereof;

(d) water-soluble sweeteners derived from naturally occurring water-soluble sweeteners, such as chlorinated derivatives of ordinary sugar (sucrose), e.g., chlorodeoxysugar derivatives such as derivatives of chlorodeoxysucrose or chlorodeoxygalactosucrose, known, for example, under the product designation of Sucralose; examples of chlorodeoxysucrose and chlorodeoxygalactosucrose derivatives include but are not limited to: 1-chloro-1'-deoxysucrose; 4-chloro-4-deoxy-alpha-D-galactopyranosyl-alpha-D-fructofuranoside, or 4-chloro-4-deoxygalactosucrose; 4-chloro-4-deoxy-alpha-D-galactopyranosyl-1-chloro-1-deoxy-beta-D-fructofuranoside, or 4,1'-dichloro-4,1'-dideoxygalactosucrose; 1',6'-dichloro1',6'-dideoxysucrose; 4-chloro-4-deoxy-alpha-D-galactopyranosyl-1,6-dichloro-1,6-dideoxy-beta-D-fructofuranoside, or 4,1',6'-trichloro-4,1',6'-trideoxygalactosucrose; 4,6-dichloro-4,6-dideoxy-alpha-D-galactopyranosyl-6-chloro-6-deoxy-beta-D-fructofuranoside, or 4,6,6'-trichloro-4,6,6'-trideoxygalactosucrose; 6,1',6'-trichloro-6,1',6'-trideoxysucrose; 4,6-dichloro-4,6-dideoxy-alpha-D-galactopyranosyl-1,6-dichloro-1,6-dideoxy-beta-D-fructofuranoside, or 4,6,1',6'-tetrachloro4,6,1',6'-tetradeoxygalacto-sucrose; and 4,6,1',6'-tetradeoxy-sucrose, and mixtures thereof;

(e) protein based sweeteners such as thaumaoccous danielli (Thaumatin I and II) and talin;

(f) the sweetener monatin (2-hydroxy-2-(indol-3-ylmethyl)-4-aminoglutaric acid) and its derivatives; and (g) the sweetener Lo han guo (sometimes also referred to as "Lo han kuo").

The intense sweetening agents may be used in many distinct physical forms well-known in the art to provide an initial burst of sweetness and/or a prolonged sensation of sweetness. Without being limited thereto, such physical forms include free forms, such as spray dried, powdered, beaded forms, encapsulated forms, and mixtures thereof.

Flavoring agents, which can vary over a wide range, may be selected in amounts from about 0.1% to 10.0% by weight, preferably from about 0.5% to 5.0% by weight. Flavoring agents for use in chewing gum compositions are well known and include citrus oils, peppermint oil, spearmint oil, oil of wintergreen, menthol, cinnamon, ginger and the like.

Other materials, which may be present in the chewing gum composition of the present invention, include antioxidants (e.g. butylated hydroxyanisole, butylated hydroxytoluene, beta-carotenes, tocopherols), colorants, flavoring agents and the like.

The chewing gum products may be prepared using standard techniques and equipment known to those skilled in the art. The apparatus useful in accordance with the embodiments described herein includes mixing and heating apparatus well known in the chewing gum manufacturing arts, and therefore the selection of the specific apparatus will be apparent to the artisan. For general chewing gum preparation processes see U.S. Pat. No. 4,271,197 to Hopkins et al, U.S. Pat. No. 4,352,822 to Cherukuri et al and U.S. Pat. No. 4,497,832 to Cherukuri et al, each of which is incorporated herein by reference in its entirety.

Coating techniques for applying a coating for a chewing gum composition such as pan and spray coating are well known. Some embodiments include coating with solutions adapted to build a hard candy layer. Both sugar and sugar alcohols may be used for this purpose together with high intensity sweeteners, colorants, flavoring agents, binders and other conventional additives.

The sweetener may be present in an amount of from about 30% to 80% by weight of the coating syrup. A binder such as magnesium stearate may be added to the coating syrup in an amount of from about 1% to 15% by weight of the coating syrup to enhance or promote adhesion. Optionally, minor amounts of conventional additives may also be present. The sweeteners suitable for use in the coating syrup include sugarless sweeteners such as the polyhydric alcohols, e.g., xylitol, sorbitol, mannitol, and mixtures, thereof; as well as maltitol, isomaltitol, hydrogenated starch hydrolysates, and hydrogenated glucose syrups. Mono, di- and polysaccharide may also be included. For example, sugars such as sucrose, fructose, glucose, galatose and maltose may also be employed as a sweetener. Other sweeteners suitable for use in the coating syrup include, but are not limited to, free saccharin acid, water soluble salts of saccharin, cyclamate salts, palatinit dihydrochalcones, glycyrrhizin, L-aspartyl-L-phenylalanine methyl ester, amino acid based sweeteners, talin, steviosides, dihydrochalcone compounds, acesulfame salts and mixtures thereof.

Other ingredients may be added in minor amounts to the coating syrup and include moisture absorbing compounds, anti-adherent compounds, dispersing agents and film forming agents. The moisture absorbing compounds suitable for use in the coating syrups include mannitol or dicalcium phosphate. Examples of useful anti-adherent compounds, which may also function as filler, include talc, magnesium trisilicate and calcium carbonate. These ingredients may be employed in amounts of about 0.5% to 5% by weight of the syrup. Examples of dispersing agents, which may be employed in the coating syrup, include titanium dioxide, talc or other anti-adherent compounds as set forth above.

The coating syrup is usually heated and a portion thereof deposited on the chewing gum cores. Usually a single deposition of the coating syrup is not sufficient to provide the desired amount or thickness of coating and it usually will be necessary to apply second, third or more coats of the coating syrup in order to build up the weight and thickness of the coating to desired levels with layers allowed to dry in-between coats.

In some embodiments of the chewing gum composition, the heating and cooling agents or warming composition are added to the coating. These components may be applied subsequent to the syrup coating. Further details regarding the preparation of chewing gum compositions can be found in Skuse's Complete Confectioner (13th Edition) (1957) including pp. 41-71, 133-144, and 255-262; and Sugar Confectionery Manufacture (2nd Edition) (1995), E. B. Jackson, Editor, pp. 258-286, the contents of which is incorporated herein by reference.

Confectionery Compositions

In some embodiments, the warming or heating compositions described above are used in confectioneries. Compositions of confectionaries are well known in the art and described in depth in, for instance, U.S. Pat. Nos: 6,685,916, 6,627,233 and 6,696,044, referred to above.

The term "confectioneries" as used herein includes, but is not limited to: nougats, candies, panned goods, gel confections, fondants, chewy candies, gummy candies, lozenges, hard boiled candies, centerfill confections, mints, troches, pastilles, microcapsules, and fast-dissolving solid forms including freeze dried forms (cakes, wafers, thin films, and tablets) and fast dissolving solid forms including compressed tablets. The term "fast dissolving solid form" as used herein means that the solid dosage form dissolves in less than about 60 seconds, desirably less than about 15 seconds, more desirably less than about 5 seconds, in the oral cavity. Lozenges include discoid shaped solids, which may include a flavored base. The base may be a hard sugar candy, glycerinated gelatin, or combination of sugar with sufficient mucilage to give it form. Compressed tablet forms typically include one or more fillers (compressible sugar), flavoring agents and lubricants. As used herein, the term "confectioneries" can also include fat-based confections such as chocolate, milk chocolate, dark chocolate, white chocolate, and combinations thereof.

Confectionery compositions may include a confectionery base and any of the warming or heating compositions described above. The confectionery compositions also may include a variety of optional additives, as provided in more detail below. Upon consumption, the warming or heating composition releases from the confection and imparts an enhanced and longer-lasting heating sensation than that provided by the composition in the absence of the cooling agent.

A confectionery base may include bulk sweeteners such as sugars and sugarless bulk sweeteners, or the like, or mixtures thereof. Bulk sweeteners generally are present in amounts of about 0.05% to about 99% by weight of the composition.

A variety of traditional ingredients also may be included in the confectioneries in effective amounts such as coloring agents, antioxidants, preservatives, sweeteners, and the like. Coloring agents may be used in amounts effective to produce the desired color. The coloring agents may include pigments which may be incorporated in amounts up to about 6%, by weight of the composition. For example, titanium dioxide may be incorporated in amounts up to about 2%, and preferably less than about 1%, by weight of the composition. The colorants may also include natural food colors and dyes suitable for food, drug and cosmetic applications. These colorants are known as F.D.& C. dyes and lakes. The materials acceptable for the foregoing uses are preferably water-soluble. Illustrative nonlimiting examples include the indigoid dye known as F.D.& C. Blue No. 2, which is the disodium salt of 5,5-indigotindisulfonic acid. Similarly, the dye known as F.D.& C. Green No. 1 comprises a triphenylmethane dye and is the monosodium salt of 4-[4-(N-ethyl-p-sulfoniumbenzylamino) diphenylmethylene]-[1-(N-ethyl-N-p-sulfoniumbenzyl)-delta-2,5-cyclohexadieneimine]. A full recitation of all F.D.& C. colorants and their corresponding chemical structures may be found in the Kirk-Othmer Encyclopedia of Chemical Technology, 3rd Edition, in volume 5 at pages 857-884, which text is incorporated herein by reference.

Lubricants also may be added in some embodiments to improve the smoothness of the comestible, such as, for example hard candy embodiments. Suitable lubricants include, but are not limited to, fats, oils, aloe Vera, pectin and combinations thereof.

Similarly, in some embodiments, the comestible may have smooth edges. In such embodiments, the comestible may have any shape, such as square, circular or diamond-shaped, however, the edges are rounded to provide a smooth comestible. Another manner of lending smoothness to the comestibles is to deposit the comestible composition into moulds during the manufacturing process. Accordingly, in some embodiments, the comestible is deposited, as described in more detail below.

Other conventional additives known to one having ordinary skill in the art also may be used in the confectionery compositions.

In some embodiments, confectionery compositions may be produced by batch processes. Such confections may be prepared using conventional apparatus such as fire cookers, cooking extruders, and/or vacuum cookers. In some embodiments, the bulk sweetener (sugar or sugar free) and a solvent (e.g., water), are combined in a mixing vessel to form a slurry. The slurry is heated to about 70° C. to 120° C. to dissolve any sweetener crystals or particles and to form an aqueous solution. Once dissolved, heat and vacuum are applied to cook the batch and boil off water until a residual moisture of less than about 4% is achieved. The batch changes from a crystalline to an amorphous, or glassy, phase. The warming or heating composition then may be admixed in the batch by mechanical mixing operations, along with any other optional additives, such as coloring agents, flavorants, and the like. The batch is then cooled to about 50° C. to 10° C. to attain a semi-solid or plastic-like consistency.

The optimum mixing required to uniformly mix the components during manufacturing of hard confectionery is determined by the time needed to obtain a uniform distribution of the materials. Normally, mixing times of from four to ten minutes have been found to be acceptable. Once the candy mass has been properly tempered, it may be cut into workable regions or formed into desired shapes having the correct weight and dimensions. A variety of forming techniques may be utilized depending upon the shape and size of the final product desired. Once the desired shapes are formed, cool air is applied to allow the comestibles to set uniformly, after which they are wrapped and packaged.

Alternatively, various continuous cooking processes utilizing thin film evaporators and injection ports for incorporation of ingredients including the warming or heating compositions are known in the art and may be used as well.

The apparatus useful in accordance with some embodiments comprise cooking and mixing apparatus well known in the confectionery manufacturing arts, and selection of specific apparatus will be apparent to one skilled in the art.

Additionally, in some embodiments, various confectionery configurations with multiple regions may be employed. These configurations may include, but are not limited to, liquid center-fill, powder center-fill, hard coated, soft coated, laminated, layered and enrobed. In some embodiments, the warming or heating composition may be included in one region or in multiple regions of the product.

Confectionery compositions in the form of pressed tablets such as mints may generally be made by combining finely sifted sugar or sugar substitute, flavoring agent (e.g. peppermint flavor), bulking agent such as gum arabic, and an optional coloring agent. The flavoring agent and the bulking agent are combined and then gradually the sugar or sugar substitute are added along with a coloring agent, if needed.

The product is then granulated by passing through a sieve of desired mesh size (e.g. 12 mesh) and then dried at typically 55° C. to 60° C. The resulting powder is fed into a tableting machine fitted with a large size punch and the resulting pellets are broken into granules and then pressed.

Hard boiled candies typically contain sugar or sugar substitute, glucose, water, flavoring agent and optional coloring agent. The sugar is dissolved in the water and glucose is then added. The mixture is brought to a boil. The resulting liquid to which may previously have been added a coloring agent is poured onto an oiled slab and cooled. The flavoring agent is then added and kneaded into the cooled mass. The resulting mixture is then fed to a drop roller assembly known in the art to form the final hard candy shape.

A nougat composition typically includes two principal ingredients, a high boiled candy and a frappe. By way of example, egg albumen or substitute thereof is combined with water and whisked to form a light foam. Sugar and glucose are added to water and boiled typically at about 130° C. to 140° C. and the resulting boiled product is poured into a mixing machine and beat until creamy. The beaten albumen and flavoring agent are combined with the creamy product and the combination is thereafter thoroughly mixed.

Further details regarding the preparation of confectionery compositions can be found in Skuse's Complete Confectioner (13th Edition) (1957) including pp. 41-71, 133-144, and 255-262; and Sugar Confectionery Manufacture (2nd Edition) (1995), E. B. Jackson, Editor, pp. 129-168, 169-188, 189-216, 218-234, and 236-258, the contents of which are incorporated herein by reference.

Soft Confectionery Compositions

In some embodiments, the orally delivered product may be in the form of various soft confectionery formats. Soft confectionery formats may include, but are not limited to, nougat, caramel, taffy, gummies and jellies.

Soft confectionery compositions may include a confectionery base and any of the warming compositions described above, which may include at least one warming agent and at least one cooling agent. The soft confectionery compositions also may include a variety of optional additives, such as any of the additives set forth above in the section describing confectionery compositions. Upon consumption, the warming composition releases from the soft confection and provides an enhanced and/or longer-lasting heating sensation than the composition in the absence of the cooling agent(s).

Some soft confectionery compositions include nougat compositions, which may include two principal components, a high-boiled candy and a frappe. By way of example, egg albumen or substitute thereof is combined with water and whisked to form a light foam. Sugar and glucose are added to water and boiled typically at temperatures of from about 130° C. to 140° C. and the resulting boiled product is poured into a mixing machine and beaten until creamy. The beaten albumen and flavoring agent are combined with the creamy product and the combination is thereafter thoroughly mixed.

In some embodiments, a caramel composition may include sugar (or sugar substitute), corn syrup (or polyol syrup), partially hydrogenated fat, milk solids, water, butter, flavors, emulsifiers, and salt. To prepare the caramel, the sugar/sugar substitute, corn syrup/polyol syrup, and water may be mixed together and dissolved over heat. Then, the milk solids may be mixed in to the mass to form a homogeneous mixture. Next, the minor ingredients may be mixed in with low heat. The heat then may be increased to boiling. Once sufficient water is removed and color/flavor developed, the mass may be cooled somewhat and temperature sensitive ingredients may be mixed in prior to discharging and forming/shaping/wrapping the finished product.

In some embodiments, a taffy composition may include sugar (or sugar substitute), corn syrup (or polyol syrup), partially hydrogenated fat, water, flavors, emulsifiers, and salt. The process for preparing taffy can be similar to that for caramel and, optionally, the final taffy mass may be pulled to develop its desired texture.

In some embodiments, a gummi composition may include sugar (or sugar substitute), corn syrup (or polyol syrup), gelatin (or suitable hydrocolloid), flavor, color, and optionally acid. The gummi may be prepared by hydrating the gelatin or suitable hydrocolloid, heating the sugar/corn syrup (sugar substitute/polyol syrup) and combining the two components with heat. Once the combined mixture reaches its final temperature or suitable sugar solids level, components such as flavor, color, and the like may be incorporated into the mixture and then poured into molds prior to cooling, wrapping, and finishing. Various surface treatments such as applications of wax or fat can be applied to decrease sticking.

In some embodiments, a jelly composition may include a starch-based jelly or a pectin-based jelly. As with gummis, jelly products may be produced by hydrating the hydrocolloid and combining the hydrated mixture with a cooked syrup component. The mixture then may be cooked to a final moisture content and minor components may be incorporated. As with gummis, jelly candies may be poured into molds such as starch molds. As with gummis, surface treatments, such as fats or waxes, may be applied. Additionally, jelly candies may have dry surface treatments, such as applications of sanding sugar, acid, non-pareils, and the like.

Additionally, in some embodiments, various soft confectionery configurations with multiple regions may be employed. These configurations may include, but are not limited to, liquid center-fill, powder center-fill, hard coated, soft coated, laminated, layered and enrobed. In some embodiments, the warming composition may be included in one region or in multiple regions of the product.

Chocolate Confectionery Compositions

In some embodiments, the orally delivered product may be in the form of various chocolate confectionery formats. Chocolate confectioneries can include milk chocolate, dark chocolate, and/or white chocolate. Milk chocolate can include milk solids with other milk chocolate ingredients such as cocoa liquor, cocoa butter and/or other fats, sweeteners, emulsifiers, flavors, and the like. In some embodiments, the milk solids can be in an amount of 5% by weight of the milk chocolate composition to amounts of greater than 40% by weight of the milk chocolate composition. The milk solids can be in the form of dry milk powder or liquid milk.

Dark chocolate can include ingredients as in milk chocolate but may have little to no milk solids components. White chocolate can include ingredients such as fats, sweeteners, flavors, emulsifiers, and the like but does not contain cocoa liquor. White chocolate is also referred to as compound coating.

Suitable methods for combining chocolate ingredients are well known to those skilled in the art, and include for example a food grade blender, a mixer, etc.

The present warming compositions will now be illustrated in greater detail with reference to the following Examples in view of the Comparative Examples, but it should be understood that the warming compositions are not limited thereto. Unless otherwise noted, all the percents are by weight.

EXAMPLES

Example 1

Warming compositions are prepared including warming and cooling agents in the amounts indicated in Table 1. As shown in Table 1, the warming agents include ginger, Vanillyl Butyl Ether (VBE), capsicum oleoresin and piperine. The cooling agents shown in Table 1 include menthol, N,2,3-trimethyl-2-isopropyl butanamide (WS-23) and N-ethyl-p-menthane-3-carboxamide (WS-3). In Table 1, inventive warming compositions include Compositions A, C and D. The comparative composition shown in Table 1 is Composition B, which does not include the addition of a cooling agent.

TABLE 1

Heating or Warming Compositions A-D

| Component | Weight % | | | |
|---|---|---|---|---|
| | A | B | C | D |
| Ginger | 3-4 | 0 | 0 | 2-4 |
| Vanillyl Butyl Ether | 35-75 | 45-85 | 20-30 | 65-75 |
| Capsicum Oleoresin | 20-25 | 22-35 | 40-50 | 20-25 |
| piperine | 0.05-0.12 | 0.075-0.35 | 20-30 | 0.000015-0.000030 |
| Menthol | 0.2-1.2 | 0 | 0 | 0.5-1.2 |
| WS-23 | 0 | 0 | 0.02-0.30 | 0 |
| WS-3 | 0 | 0 | 0 | 0.02-0.30 |
| Total | 100% w/w | 100% w/w | 100% w/w | 100% w/w |

The inventive warming compositions provided in Table 1 above (Compositions A, C and D) can be incorporated into chewing gum compositions to provide chewing gums having an enhanced and/or longer-lasting heating sensation. In particular, all four of the warming compositions (Compositions A-D) from Table 1 above are added to chewing gum compositions in the amounts indicated in Table 2 below. Specifically, in Table 2, Inventive Chewing gum Compositions A, C and D include inventive warming Compositions A, C and D, respectively from Table 1. Comparative Chewing gum Composition B includes comparative warming Composition B from Table 1, which does not include the addition of a cooling agent.

TABLE 2

Chewing gum Compositions A-D Including Heating or Warming Compositions

| Component | % By Weight | | | |
|---|---|---|---|---|
| | A | B | C | D |
| Chewing gum Base Components | 22-45 | 22-45 | 22-45 | 22-45 |
| Lecithin | 0.1-0.3 | 0.1-0.3 | 0.1-0.3 | 0.1-0.3 |
| Sorbitol | 40-60 | 40-60 | 40-60 | 40-60 |
| Glycerin | 1-5 | 1-5 | 1-5 | 1-5 |
| Composition A from Table 1 | 0.1-0.3 | 0 | 0 | 0 |
| Composition B from Table 1 | 0 | 0.1-0.3 | 0 | 0 |
| Composition C from Table 1 | 0 | 0 | 0.1-0.3 | 0 |
| Composition D from Table 1 | 0 | 0 | 0 | 0.1-0.3 |
| Other Components | | | | |
| Ginger - Clove Flavor | 2.3-3.4 | 2.3-3.4 | 2.3-3.4 | 2.3-3.4 |
| Sucralose | 0.03-0.06 | 0.03-0.06 | 0.03-0.06 | 0.03-0.06 |
| Aspartame | 0.01-0.05 | 0.01-0.05 | 0.01-0.05 | 0.01-0.05 |
| Acesulfame-K | 0.01-0.05 | 0.01-0.05 | 0.01-0.05 | 0.01-0.05 |
| Total | 100 | 100 | 100 | 100 |

The chewing gums of Compositions A, C and D will provide an enhanced and/or longer lasting heating sensation upon consumption as compared to the chewing gum of Comparative Composition B due to the incorporation of the cooling agents in addition to the warming agents in Compositions A, C and D.

From the foregoing description, various modifications and changes in the compositions and methods will occur to those skilled in the art. All such modifications coming within the scope of the appended claims are intended to be included therein.

All publications, including but not limited to patents and patent applications, cited in this specification are herein incorporated by reference as if each individual publication were specifically and individually indicated to be incorporated by reference herein as though fully set forth.

What is claimed is:

1. A warming or heating oral composition comprising:
   (a) a warming agent comprising:
      (i) vanillyl butyl ether in an amount of about 15% to about 80% by weight of said composition;
      (ii) capsicum oleoresin in an amount of about 15% to about 55% by weight of said composition; and
      (iii) piperine in an amount of about 0.00001% to about 35% by weight of said composition; and
   (b) at least one cooling agent comprising:
      (i) menthol in an amount of about 0.2% to about 2% by weight of said composition;
      (ii) N,2,3-trimethyl-2-isopropyl butanamide in an amount of about to 0.02% to about 1% by weight of said composition; and
      (iii) N-ethyl-p-menthane-3-carboxamide in an amount of about 0.02% to about 1% by weight of said composition, wherein said composition provides an enhanced and longer lasting heating sensation as compared to the heating sensation provided by the composition in the absence of the at least one cooling agent.

2. The composition according to claim 1, wherein the warming agent further comprises ginger, wherein the ginger is present in an amount of about 2% to about 4% by weight of said composition.

3. The composition according to claim 1, wherein the menthol is present in an amount of about 0.2% to about 1.2% by weight of said composition.

4. The composition according to claim 1, wherein the N,2,3-trimethyl-2-isopropyl butanamide is present in an amount of about 0.02% to about 0.3% by weight of said composition.

5. The composition according to claim 1, wherein the N-ethyl-p-menthane-3-carboxamide is present in an amount of about 0.02% to about 0.3% by weight of said composition.

6. The composition according to claim 1, wherein the composition further comprises a salty taste providing ingredient, a food acid, or combinations thereof.

7. The composition according to claim 1, wherein the warming agent further comprises ginger, wherein the ginger is present in an amount of up to about 5% by weight of said composition.

* * * * *